US00PP12008P2

(12) United States Plant Patent
Zaiger et al.

(10) Patent No.: US PP12,008 P2
(45) Date of Patent: Jul. 24, 2001

(54) NECTARINE TREE NAMED 'HONEY ROYALE'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/480,625

(22) Filed: Jan. 10, 2000

(51) Int. Cl.[7] ..... A01H 5/00

(52) U.S. Cl. ..... Plt./192

(58) Field of Search ..... Plt./192

*Primary Examiner*—Bruce R. Campell
*Assistant Examiner*—June Hwu

(57) ABSTRACT

A new and distinct variety of nectarine tree (*Prunus persica* var. *nucipersica*), which has the following unique combination of desirable features, that are outstanding in a new variety. The following features of the tree and its fruit are characterized with the tree budded on Nemaguard Rootstock (non-patented), grown on Hanford sandy loam soil, with Storie Index rating 95, in USDA Hardiness Zone 9, near Modesto, Calif., and with standard commercial cultural fruit growing practices such as pruning, thinning, spraying, irrigation and fertilization:

1. Heavy and regular production of fruit.
2. Fruit with a high degree of attractive red skin color.
3. Fruit with a mild, sweet, sub-acid flavor with excellent eating quality.
4. Fruit having firm flesh, good handling and shipping quality.
5. Produces relatively uniform large, yellow flesh, freestone fruit throughout the tree.
6. Fruit holding firm on the tree for 2 weeks after maturity (shipping ripe).
7. Vigorous, upright growth.

1 Drawing Sheet

BACKGROUND OF THE VARIETY

In the field of plant genetics, we conduct and extensive and continuing plant-breeding program including the organization and asexual reproduction of orchard trees, of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarines and peaches known to us, and mentioned herein; Golden Supreme Peach (non-patented) and Honey Kist Nectarine (U.S. Plant Pat. No. 9,333).

ORIGIN OF THE VARIETY

The present new variety of nectarine tree (*Prunus persica* var. *nucipersica*) was developed by us in our experimental orchard located near Modesto, Calif., as a first generation cross between the selected seedling with field identification No. 77GF213, and Honey Kist Nectarine (U.S. Plant Pat. No. 9,333). The nectarine seedling 77GF213 (non-patented), which is the maternal parent, was selected for future use in our breeding program, and originated from a cross of a nectarine seedling selection of unknown parentage, with Golden Supreme Peach (non-patented). We planted and maintained under close observation, a large group of these first generation seedlings growing on their own root system. One seedling, which is the present variety, exhibited the outstanding fruit characteristics described within and was selected in 1994 for asexual reproduction and commercialization.

ASEXUAL REPRODUCTION OF THE VARIETY

Asexual reproduction of the new and distinct variety of nectarine tree was by budding to Nemaguard Rootstock (non-patented), the standard rootstock for nectarines in California, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

A new and distinct variety of nectarine tree, which is of large size, vigorous, upright growth and a regular and productive bearer of large, freestone, yellow flesh fruit with excellent flavor and eating quality. The fruit is further characterized by having firm flesh with good handling and shipping quality, the flesh being moderately juicy with a mild, sweet, sub-acid flavor, with the ability to hold firm on the tree for 2 weeks after maturity (shipping ripe), and having a high degree of attractive red skin color. In comparison to the Honey Kist Nectarine (U.S. Plant Pat. No. 9,333), which has a similar mild, sweet, sub-acid flavor, the new variety produces fruit that is larger in size and is approximately 25 days later in maturity.

PHOTOGRAPH OF THE VARIETY

The accompanying color photographic illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, age 6 years, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Pruned 12 to 14 feet in height and width at maturity for economical harvesting of fruit.

*Vigor.*—Vigorous. Growing 6 to 8 feet in height and 5 to 6 feet in width the first growing season. Primary scaffolds are selected and pruned to 4 to 5 feet in height during the first dormant season.

*Growth.*—Upright. The center branches are removed forming a vase shape. The weight of the fruit tends to spread the branches as the tree becomes productive.

*Productivity.*—Productive. Fruit set in two or more times the fruit desired for tree crop load. Fruit set is reduced and spaced by thinning to produce desired marketable size. Amount of fruit set varies with climatic conditions and cultural practices during bloom period.

*Bearer.*—Regular. Has required thinning of fruit over 5 consecutive years. No alternate bearing observed.

*Form.*—Usually pruned to vase shape.

*Density.*—Medium dense. By pruning to vase shape the branches and leaves are removed from center of tree to increase air movement and sunlight throughout the tree, enhancing the uniformity of fruit color and keeping the fruit wood healthy.

*Hardiness.*—Tree grown in USDA Hardiness Zone 9. Winter chilling requirement is approximately 850 hours below 45° F. Hardy in all stone fruit growing areas of California.

Trunk:

*Size.*—Large. Circumference 24 inches, measured 12 inches above ground, on a 6 year old tree.

*Texture.*—Medium shaggy. Becomes rougher with age of tree.

*Color.*—Mouse gray to beaver brown (5-E-3) to (5-F-3), varies with age of tree.

Branches:

*Size.*—Medium. Average circumference 9 inches measured 52 inches above ground.

*Surface.*—Smooth to medium rough, varies with age of growth.

*Lenticels.*—Medium in number. Average number of 18 within a 4 square inch surface. Large size. Average length 5/32 inch. Average width 1/16 inch. Size increases as branches grow larger. Color — apricot yellow to golden yellow (5-B-6) to (5-B-8).

*Color.*—First years new growth, bile yellow to spring green (30-C-5) to (30-C-8). Older mature growth light brown to brown (6-D-4) to (6-E-6), varies with age of growth.

Leaves:

*Size.*—Large. Average length 5½ inches. Average width 1⅝ inches.

*Form.*—Lanceolate.

*Apex.*—Acuminate.

*Margin.*—Crenate.

*Thickness.*—Medium.

*Surface.*—Upper surface — smooth. Lower surface — relatively smooth except for small ridges created by midvein with spinnate veination. Veining color — pale yellowish green to greenish yellow (30-B-5) to (30-B-6).

*Petiole.*—Medium. Average length 7/16 inch. Average width 5/64 inch, grooved longitudinally. Color — pale green to yellowish green (30-B-4) to (30-B-6).

*Glands.*—Reniform. Number varies from 1 to 4. Average number 2. Medium size. Average length 3/64 inch. Average width 1/32 inch. Grayish yellow to amber yellow (4-B-4) to (4-B-6). Some glands have a reddish color (8-D-6) around the top outer edges. Color varies with age of leaf.

*Color.*—Upper surface — green to dark green (29-F-5) to (29-F-8). Lower surface — dull green to light green (29-E-5) to (29-E-6).

Flower buds:

*Size.*—Medium to large. Average length 11/16 inch, average width ½ inch four days before bloom.

*Surface texture.*—Smooth.

*Form.*—Plump, free. Varies from conic to elongate as bud development progresses. Usually one bud forms on each side of a leaf bud on previous years new growth.

*Color.*—Pink to rose pink (11-A-4) to (12-A-4).

Flowers:

*Size.*—Large, showy. Average height 45/64 inch. Average diameter 1 51/64 inch.

*Petals.*—Number — 5. Average length 31/32 inch. Average width 31/32 inch. Alternately arranged with sepals. Nearly orbicular, narrower at point of attachment, edges vary from smooth to slightly scalloped.

*Sepals.*—Number — 5. Average length 23/64 inch. Average width 15/64 inch. Alternately arranged with petals. Upper color — red to madder red (9-A-7) to (10-A-7). Lower color — brownish red to fox red (8-C-6) to (8-D-7). Color fades with age of flower.

*Aroma.*—Very slight.

*Pollen.*—Present, self-fertile.

*Color.*—Pale yellow to light yellow (3-A-3) to (3-A-5).

*Stamens.*—Average number per flower — 23. Average length — 21/64 inch. Filament color varies from white (11-A-1) to pale pink (11-A-3). Lighter color near anthers. Anther color — red to ruby red (12-C-7) to (12-C-8).

*Pistil.*—Number — one. Average length ½ inch, stigma approximately same height as anthers. Color varies from white to pale yellowing (4-A-1) to (4-A-3).

*Blooming period.*—Date of first bloom — Mar. 5, 1999. Date of last bloom — Mar. 13, 1999. Varies slightly with climatic conditions.

*Color.*—Pink to light pink (11-A-4) to (11-A-3). Color fades with age of flower.

Fruit:

*Maturity when described.*—Firm ripe (shipping ripe).

*Date of first picking.*—Jul. 10, 1999.

*Date of last picking.*—Jul. 19, 1999. Varies slightly with climatic conditions.

*Size.*—Average diameter axially 3 inches. Average transversely in suture plane 2⅞ inches. Average weight 235 grams. Average weight varies with fertility of the soil, amount of thinning and climatic conditions.

*Form.*—Nearly globose, slightly elongated.

*Suture.*—Shallow, extends from base to apex.

*Ventral surface.*—Nearly rounded.

*Apex.*—Very slight apical point on most fruit, varies from very slight point to slightly retuse.

*Base.*—Retuse.

*Cavity.*—Rounded to slightly elongated in suture plane. Average depth 7/16 inch. Average breadth 1 inch.

Skin:

*Thickness.*—Medium.

*Texture.*—Medium, tenacious to the flesh.

*Tendency to crack.*—None.

*Color.*—Yellow to golden yellow ground color (5-A-6) to (5-A-7). Overspread with currant red to Turkish red (10-B-8) to (10-C-8).

Stem:

*Size.*—Average length 15/32 inch. Average diameter 5/64 inch.

*Color.*—Spring green to yellowish green (30-C-7) to (30-C-8).

Flesh:

*Ripens.*—Evenly.

*Texture.*—Firm, meaty.

*Fibers.*—Few, small, tender.

*Aroma.*—Moderate.

*Amygdalin.*—Undetected.

*Eating quality.*—Excellent.

*Flavor.*—Excellent, mild, sweet, sub-acid.

*Juice.*—Moderate, sweet, sub-acid, enhances flavor.

*Brix.*— 13.1°, varies slightly with number of fruit per tree, cultural practices and climatic conditions.

*Color.*—Yellow to dark yellow (4-A-7) to (4-A-8). Pit cavity varies from red to cardinal red (10-A-8) to (10-D-8).

Stone:

*Type.*—Freestone.

*Size.*—Large. Average length 1 5/8 inches. Average width 1 inch. Average thickness 3/4 inch.

*Form.*—Obovoid.

*Base.*—Usually rounded, varies from rounded to straight.

*Apex.*—Acuminate.

*Surface.*—Irregularly furrowed toward apex, pitted toward base. Pits vary from round to elongate. Surface of ridges vary from narrow to wide. One long furrow on each side of suture.

*Sides.*—Equal to unequal, some stones are slightly larger on one side.

*Tendency to split.*—None.

*Color.*—Brown to reddish brown (8-C-7) to (8-D-7) when dry.

Use: Market. Local and long distance.

Keeping quality: Good. Held firm for 3 weeks in cold storage (38° to 42° F.) without internal breakdown or wooliness of flesh.

Shipping quality: Good. Fruit showed minimal scarring or bruising of skin or flesh during packing and shipping trials.

Plant disease: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed, during indexing of plant characteristics, with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety might be grown. The present description is that of the variety grown under the ecological conditions prevailing near Modesto, Calif.

We claim:

1. A new and distinct variety of nectarine tree, substantially as illustrated and described, which is of large size, vigorous upright growth and a regular bearer of large, yellow flesh fruit with a mild, sweet, sub-acid flavor with excellent eating quality; the fruit is further characterized by having firm flesh with good storage and shipping quality, holding firm on the tree for two weeks after maturity (shipping ripe) and, in comparison to Honey Kist Nectarine (U.S. Plant Pat. No. 9,333), which has a similar mild, sweet, sub-acid flavor, the fruit of the new variety is larger in size and is approximately 25 days later in maturity.

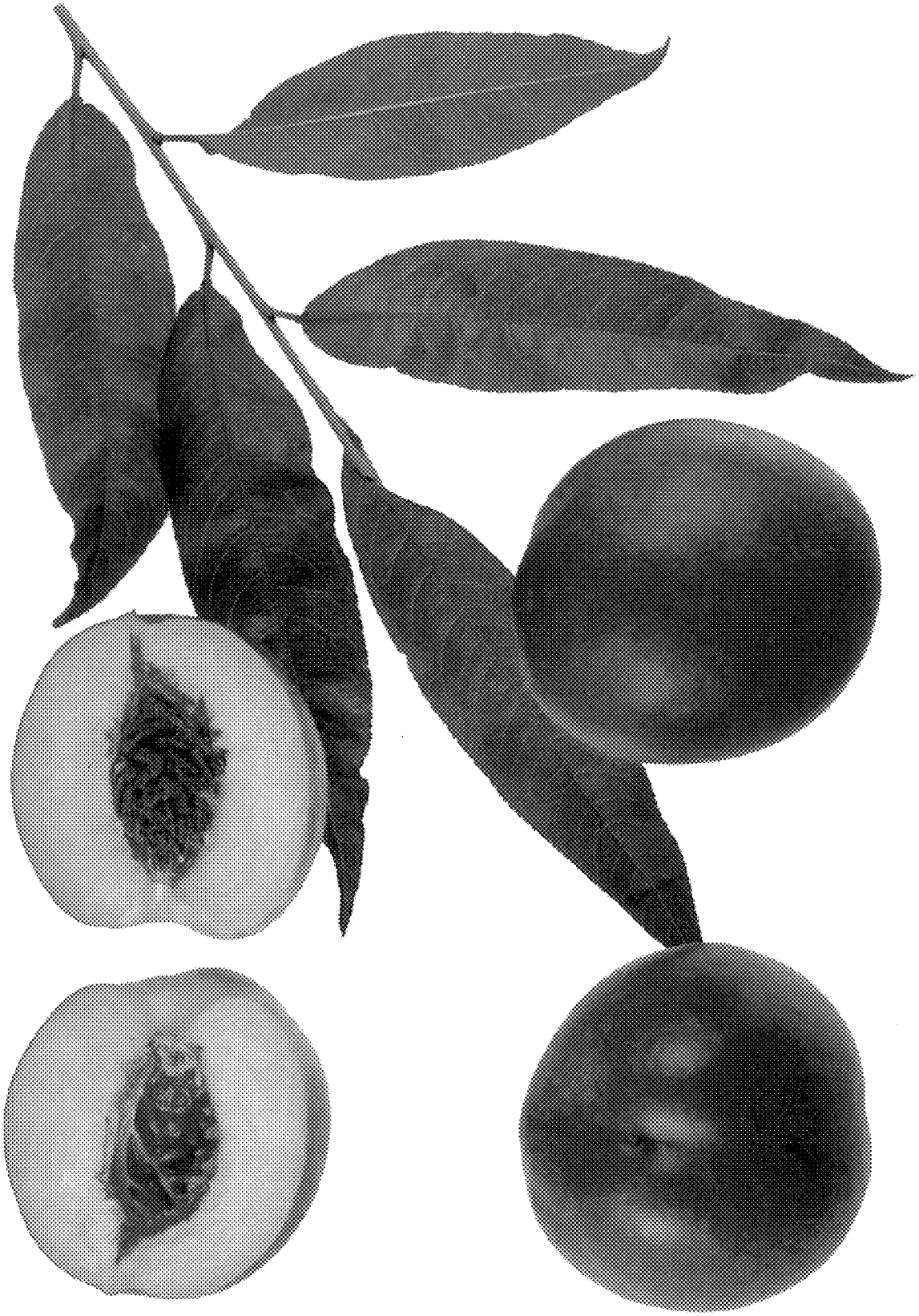

* * * * *